United States Patent [19]

Bonutti et al.

[11] Patent Number: 5,573,517
[45] Date of Patent: Nov. 12, 1996

[54] EXPANDABLE CANNULAS

[75] Inventors: Peter M. Bonutti, 1303 W. Evergreen Plz., Effingham, Ill. 62401; James S. Hawkins, Urbana, Ill.

[73] Assignee: Peter M. Bonutti, Effingham, Ill.

[21] Appl. No.: 254,368

[22] Filed: Jun. 6, 1994

Related U.S. Application Data

[62] Division of Ser. No. 13,942, Feb. 4, 1993, Pat. No. 5,320,611.

[51] Int. Cl.⁶ ................................................ A61B 17/02
[52] U.S. Cl. ........................ 604/264; 604/164; 606/198
[58] Field of Search ............................ 606/198; 604/104, 604/106, 107, 108, 109, 264, 164; 128/20

[56] References Cited

U.S. PATENT DOCUMENTS

| | | |
|---|---|---|
| 2,566,499 | 9/1951 | Richter .................................. 604/104 X |
| 3,788,318 | 1/1974 | Kim et al. . |
| 3,789,852 | 2/1974 | Kim et al. . |
| 3,811,449 | 5/1974 | Gravlee et al. . |
| 3,968,800 | 7/1976 | Vilasi ..................................... 606/198 |
| 4,320,762 | 3/1982 | Bentov ................................... 606/198 |
| 4,461,281 | 7/1984 | Carson . |
| 4,504,268 | 3/1985 | Herlitze . |
| 4,589,858 | 5/1986 | Dretler . |
| 4,630,609 | 12/1986 | Chin . |
| 4,706,670 | 11/1987 | Andersen et al. . |
| 4,716,901 | 1/1988 | Jackson et al. . |
| 4,846,812 | 7/1989 | Walker et al. . |
| 4,899,729 | 2/1990 | Gill et al. . |
| 4,954,126 | 9/1990 | Wallsten . |
| 4,966,583 | 10/1990 | Debbas . |
| 4,998,539 | 3/1991 | Delsanti . |
| 5,037,404 | 8/1991 | Gold et al. . |
| 5,069,674 | 12/1991 | Fearnot et al. . |
| 5,183,464 | 2/1993 | Dubrul et al. ..................... 606/108 X |
| 5,318,588 | 6/1994 | Horzewski et al. .................. 606/198 |

FOREIGN PATENT DOCUMENTS 184396 7/1966 U.S.S.R. ................................ 606/198

Primary Examiner—Michael H. Thaler
Attorney, Agent, or Firm—Tarolli, Sundheim, Covell, Tummino & Szabo

[57] ABSTRACT

Cannulas for surgical and medical use expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

4 Claims, 8 Drawing Sheets

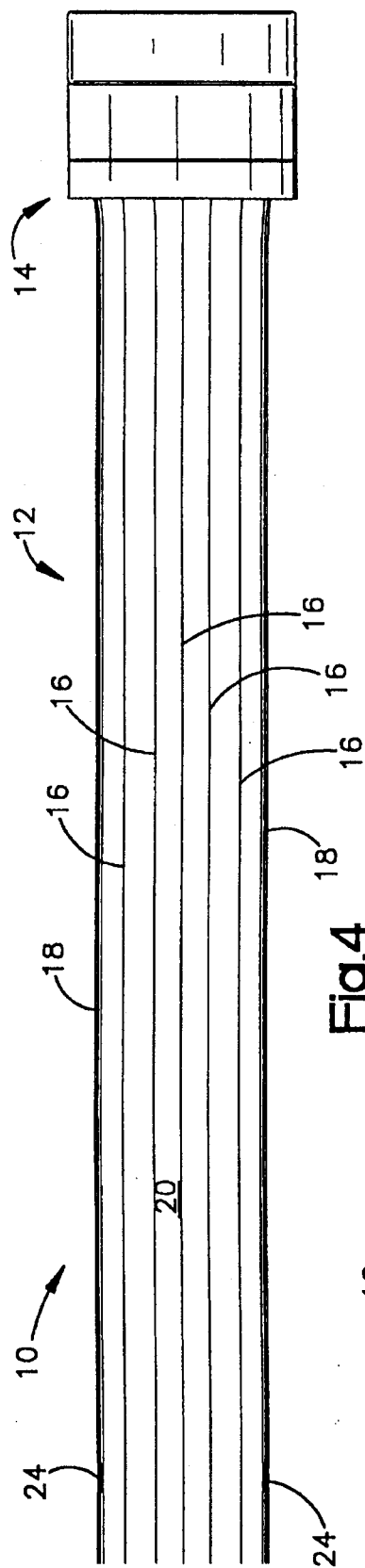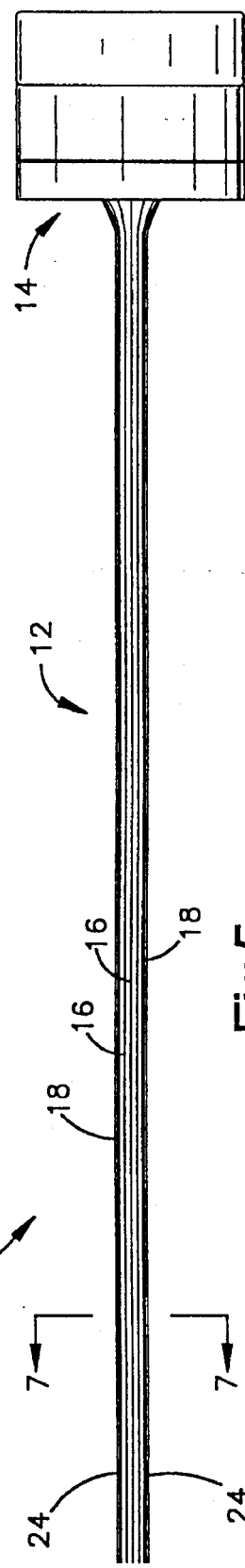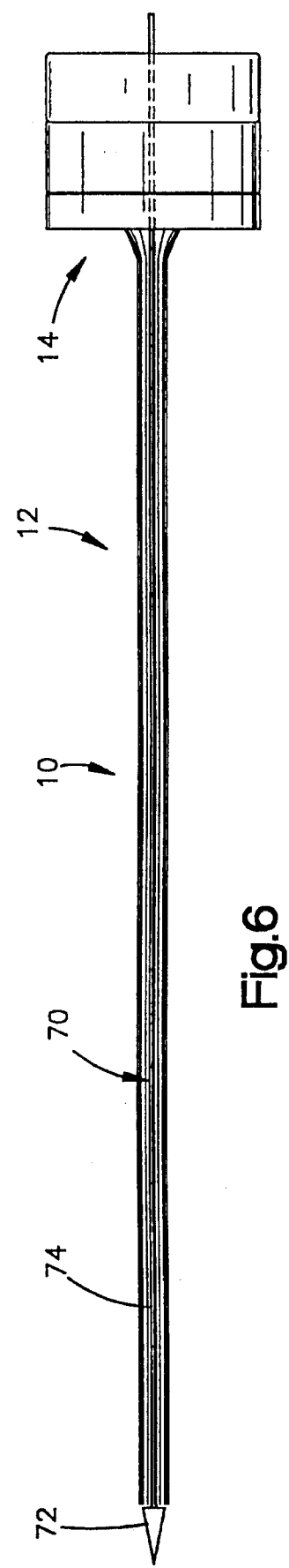

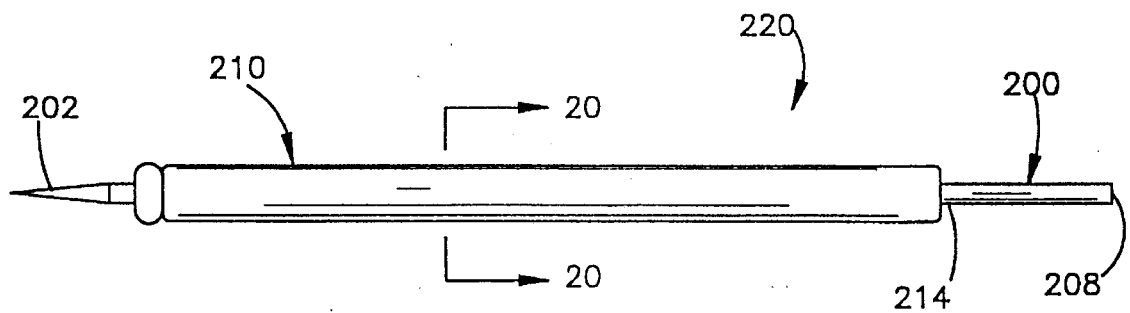
Fig.18
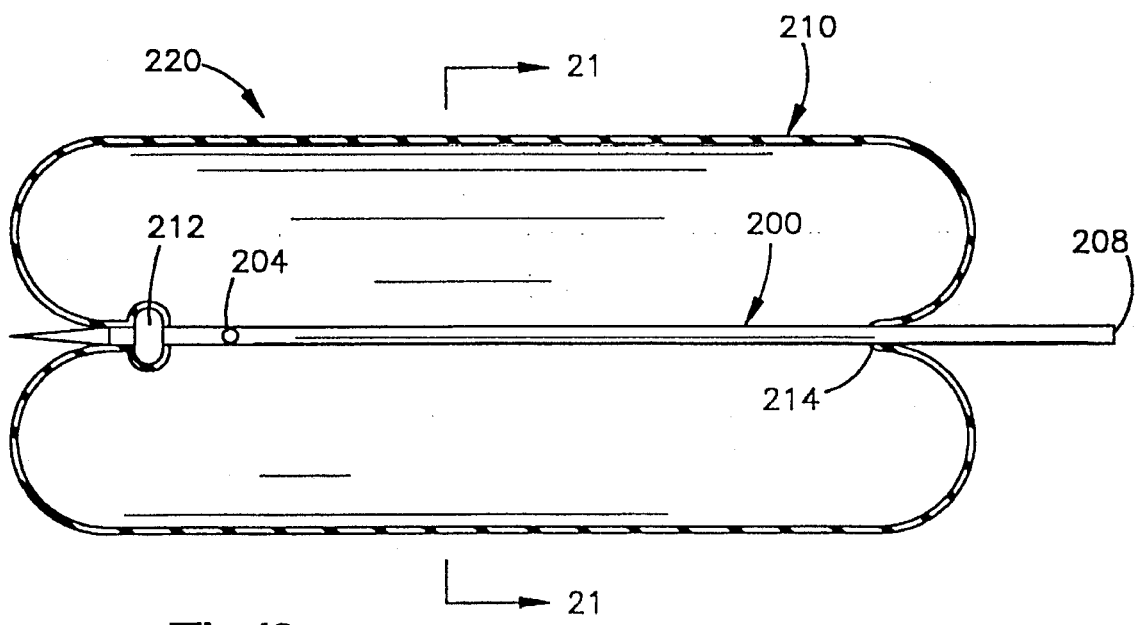
Fig.19
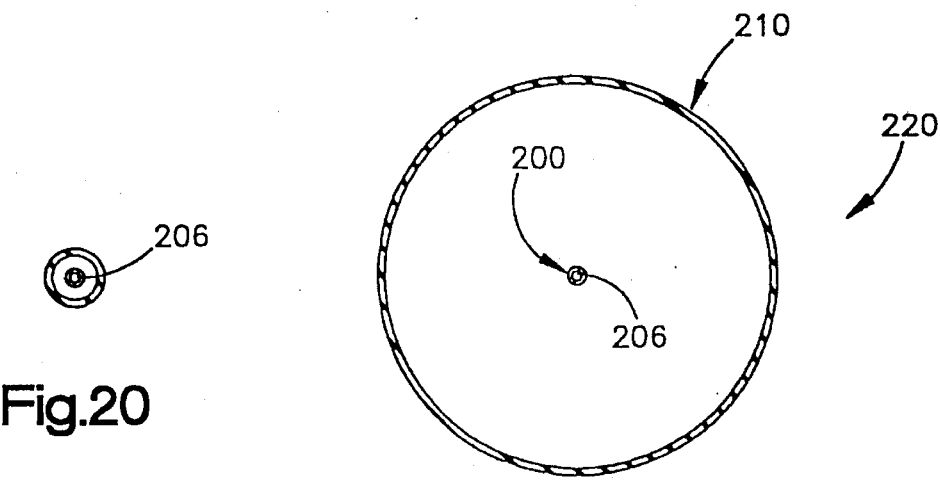
Fig.20
Fig.21

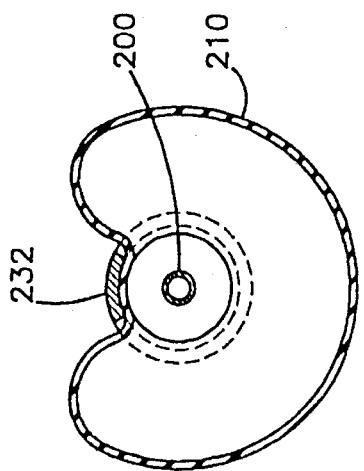
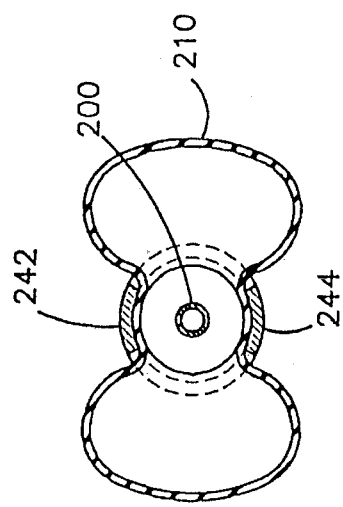
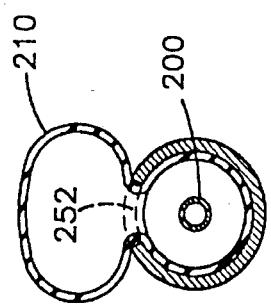
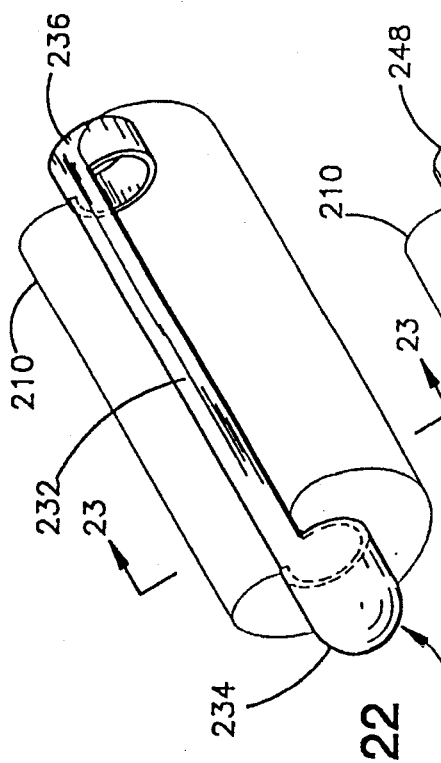
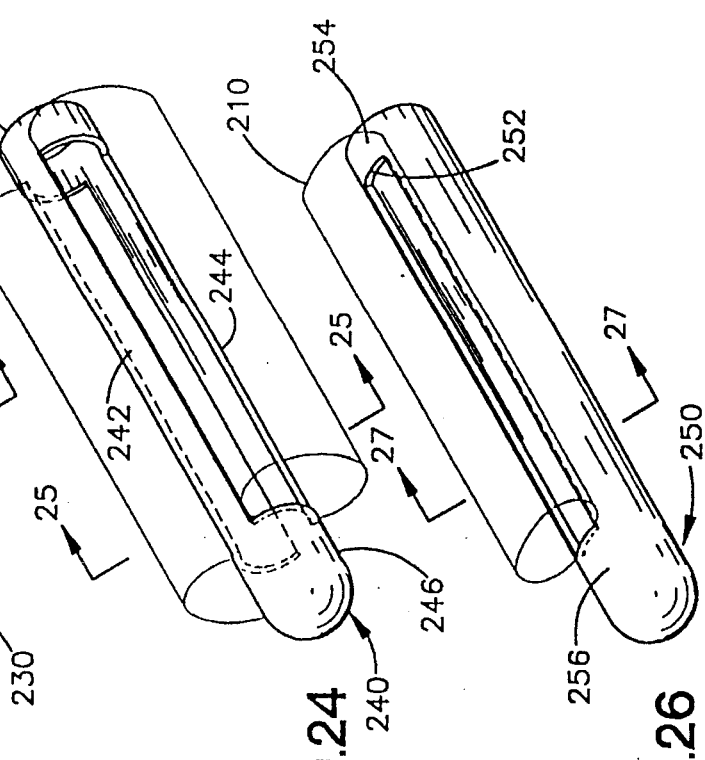

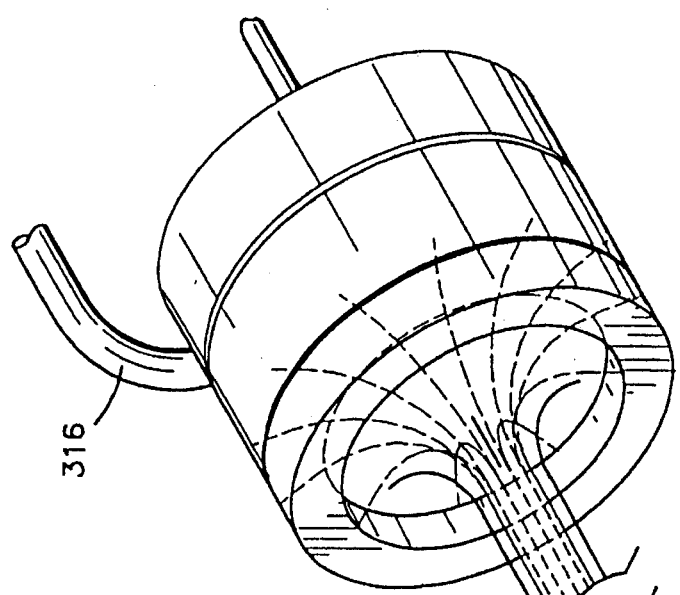
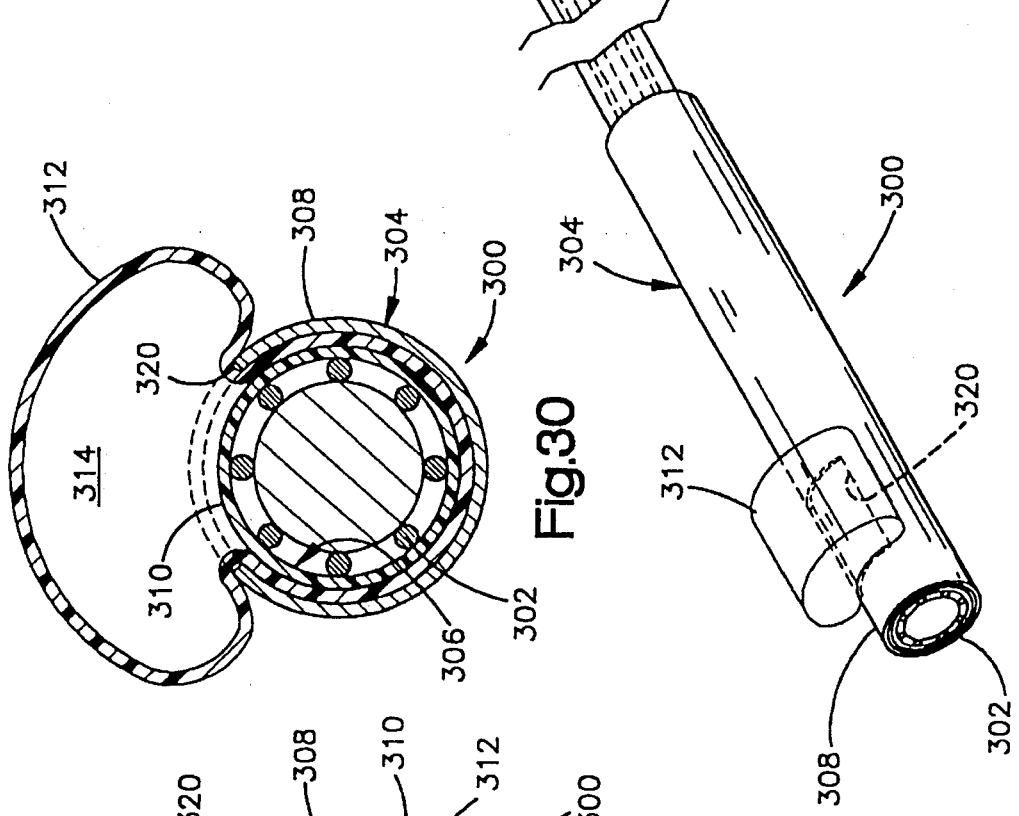
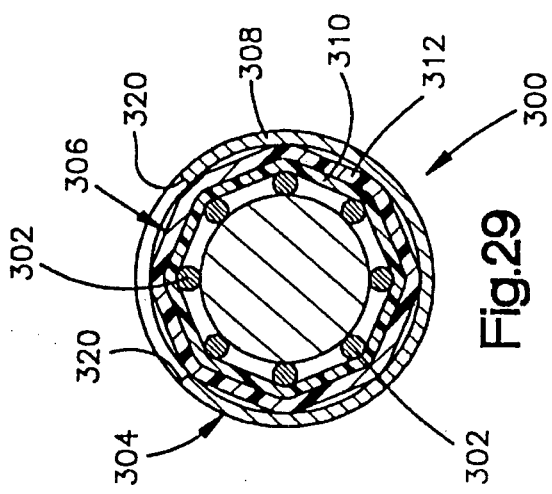

EXPANDABLE CANNULAS

This is a divisional of application Ser. No. 08/013,942 filed on Feb. 4, 1993 now U.S. Pat. No. 5,320,611.

BACKGROUND OF THE INVENTION

The present invention relates to cannulas for surgical and medical use. A typical cannula is a fixed diameter tube which a surgeon uses to maintain an instrument passage through tissue to a subcutaneous working location. The surgeon must first make an incision the full depth of the cannula in order to insert the cannula. This traumatic action damages good tissue in order to get to bad tissue. It would be desirable to provide cannulas which do not require a full depth incision, or at least require only a needle-size entrance opening, and which still allow use of a cannula to maintain an instrument passage.

SUMMARY OF THE INVENTION

In accordance with the invention, cannulas are provided which expand along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 4 is a schematic side view illustrating the cannula of FIG. 1 in an expanded condition;

FIG. 5 is a schematic side view illustrating the cannula of FIG. 1 in a contracted or collapsed condition;

FIG. 6 is a side view similar to FIG. 5 illustrating a trocar inserted in the cannula of FIG. 1;

FIG. 18 is a side elevational view of a cannula in accordance with a third embodiment of the present invention, shown in an unexpanded condition;

FIG. 19 is a longitudinal sectional view of the cannula of FIG. 18 in an expanded condition;

FIG. 20 is a sectional view taken along line 20—20 of FIG. 18;

FIG. 21 is a sectional view taken along line 21—21 of FIG. 19;

FIG. 22 shows the cannula of FIGS. 18–21 in use with a shape-controlling sleeve;

FIG. 23 is a sectional view taken along line 23—23 of FIG. 22;

FIG. 24 shows the cannula of FIGS. 18–21 in use with a second shape-controlling sleeve;

FIG. 25 is a sectional view taken along line 25—25 of FIG. 24;

FIG. 26 shows the cannula of FIGS. 18–21 in use with a third shape-controlling sleeve;

FIG. 27 is a sectional view taken along line 27—27 of FIG. 26;

FIG. 28 is a perspective view of a cannula forming another embodiment of the invention;

FIG. 29 is a sectional view of the cannula of FIG. 28, the cannula being shown in a retracted condition; and FIG. 30 is a sectional view of the cannula of FIG. 28, the cannula being shown in an expanded condition.

DESCRIPTION OF PREFERRED EMBODIMENTS

Figure 1:
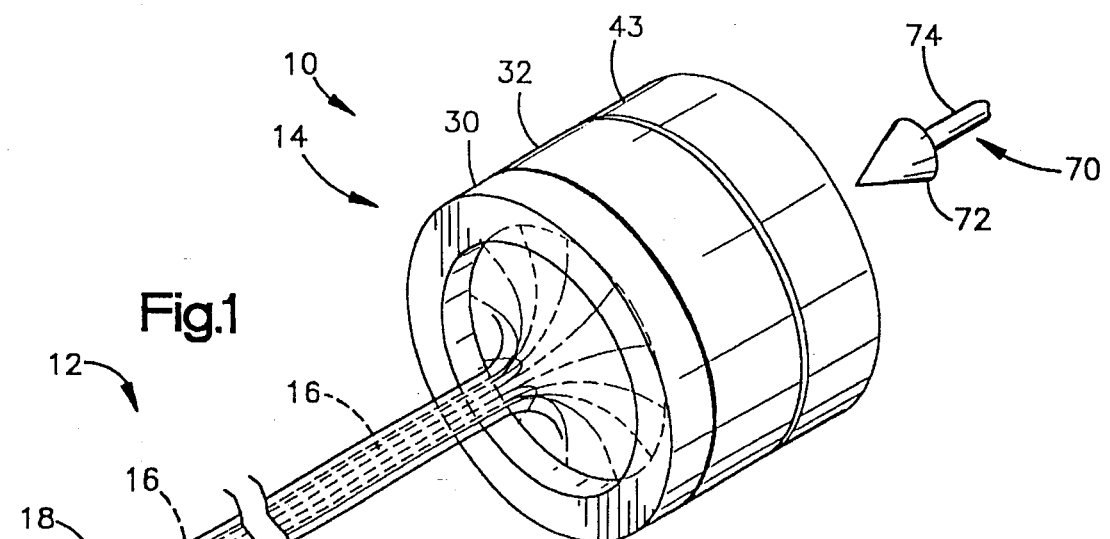
FIG. 1 is a perspective view of a cannula in accordance with a first embodiment of the invention, shown in an unexpanded condition.
Figure 2:
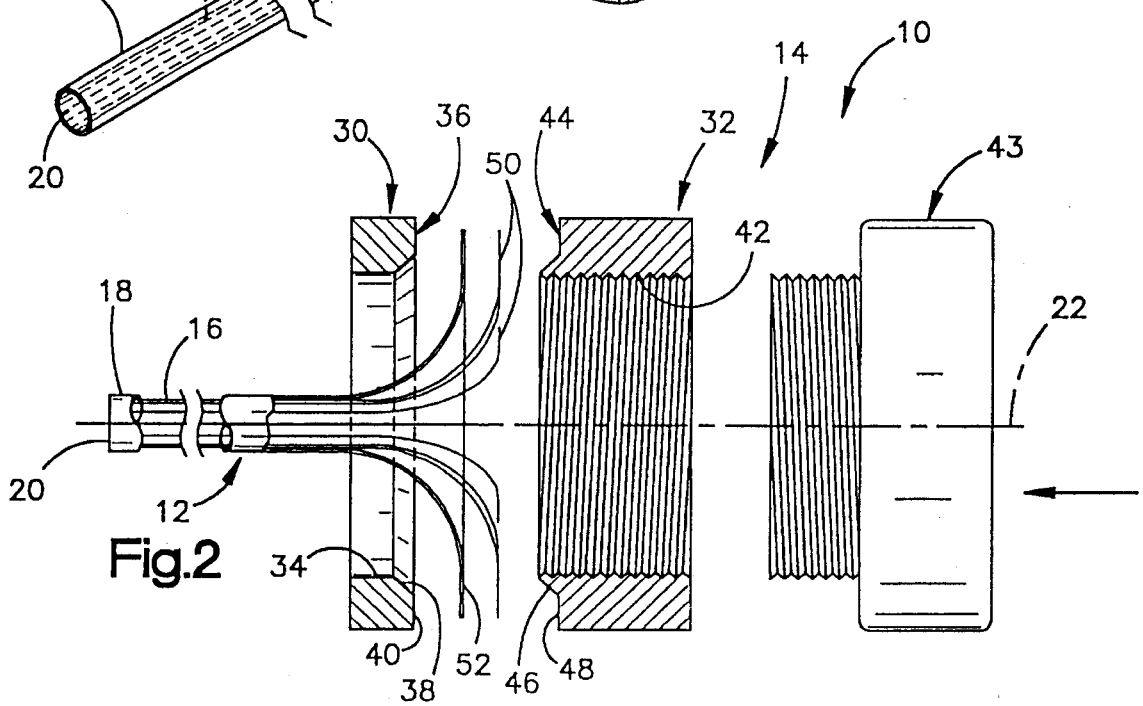
FIG. 2 is an exploded longitudinal sectional view of the cannula of FIG. 1.

In a first embodiment of the invention, a cannula 10 (FIG. 1) includes an expanding portion 12 and a proximal end portion 14. The expanding portion 12 includes a plurality of longitudinally extending wires 16. The wires 16 are surrounded for most of their length by an overlying elastic sheath 18. The wires 16 define between them a central instrument passage 20.

The wires 16 are preferably made of a material which is flexible. A preferred material is music wire, which is thin gauge steel about 0.015" in diameter. The use of the term "wire" in this application and its claims does not limit the invention to metal wires. The "wires" may also be made of other elongate material such as composites or plastics or other metals. The "wires" may also be coated.

The number of wires may be selected as desired. Applicants have found that 8 to 10 wires will suffice for a cannula expandable up to 7 mm OD, and that 12 wires or more may be necessary for a larger cannula. Ten larger diameter wires (0.025") may be used rather a larger number of small diameter wires. A greater number of wires 16 can be used if a greater diameter is needed. If not enough wires 16 are used, an instrument (trocar, insert, scope, etc.) inserted through the passage 20 when the cannula 10 is expanded will contact the elastic sheath 18 rather than the wires 16, at locations between the wires.

The wires 16 are self-aligning. When the cannula 10 is in a contracted condition, the wires 16 may overlap. When the cannula 10 is expanded, the wires 16 straighten out as shown.

The elastic sheath 18 is preferably secured to the wires 16 at both proximal and distal ends, to prevent the sheath's sliding off the wires during insertion and removal of the cannula 10. Rubber cement or cyanoacrylate or a similar adhesive can be used to bond the sheath 18 to the wires 16 as shown schematically at 24.

The elastic sheath 18 is preferably made of latex or silicone, or of C-Flex®, a general purpose thermoplastic elastomer sold by Linvatec Corporation of Clearwater, Fla. The sheath 18 is of a diameter such that it is stressed even when the cannula 10 is fully contracted. Thus, the sheath 18 constantly biases the wires 16 radially inwardly toward the axis 22 of the cannula 10.

At the proximal end portion 14 of the cannula 10, the wires 16 are clamped between an inner ring member 30 and an outer ring member 32. The inner ring member 30 has a central opening 34. The inner ring member 30 has a clamping surface 36 including a beveled edge 38 and an annular radially extending surface 40. The outer ring member 32 has a threaded central opening 42 for receiving a standard luer lock 43. The outer ring member 32 has a clamping surface 44 including a beveled edge 46 and an annular radially extending surface 48.

The ring members 30 and 32 can be made of metal, in which case they can be brazed or welded together. The ring members 30 and 32 can be made of plastic, in which case then they can be UV joined or joined by adhesive.

Figure 3:
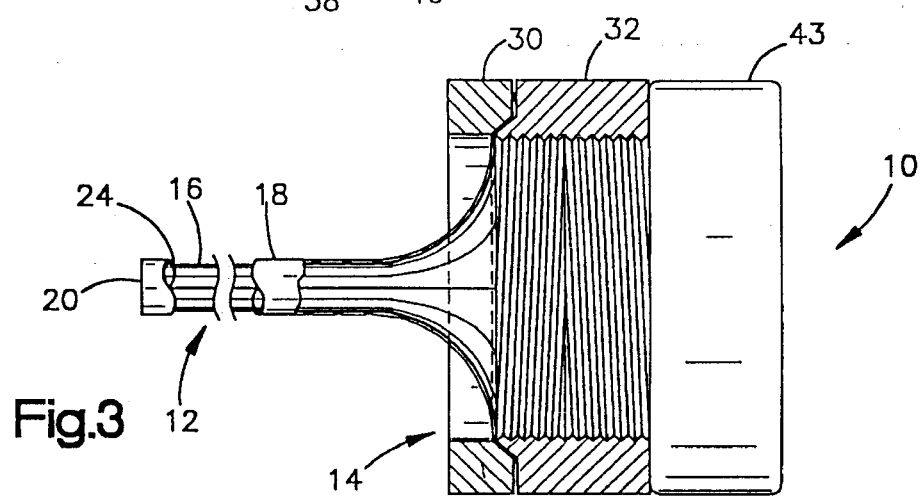
FIG. 3 is an assembled view of the cannula of FIG. 1.

Proximal end portions 50 of the wires 16 are trapped between the ring members 30 and 32. When the ring members 30 and 32 are joined together as in FIG. 3, the proximal end portions 50 of the wires 16 are trapped between the clamping surface 36 of the inner ring 30 and the clamping surface 44 of the outer ring 32. The proximal end portion 52 of the sheath 18 is preferably also trapped between the rings 30 and 32, to secure the sheath proximally. Alternatively, the proximal end portion 52 of the sheath 18 may be bonded to the wires 16 at a proximal location adjacent the ring members 30 and 32. Thus, the proximal end of the cannula expanding portion 12 is secured, having a large diameter generally equal to the expanded diameter of the cannula 10.

The sheath 18 has a circumferential outer surface 54 (FIG. 7) and a circumferential inner surface 56. The wires 16 engage the circumferential inner surface 56 of the sheath 18. The radially inner surfaces 60 of the wires 16 define an annular periphery 62 within which any item inserted in the cannula 10 is disposed. In one embodiment which has been constructed, when contracted, the cannula 10 is about 2 mm diameter, the size of a 14ga needle. Thus, the cannula 10 can possibly be inserted as a needle, clearing its own path, and not needing a trocar first. The constructed cannula is about 90 mm long. Other useful sizes include (i) up to 2.5 mm diameter with a 70 mm length; (ii) up to 7 mm diameter with a 110 mm length; and (iii) up to 11 mm diameter with a 160 mm length.

In use of the cannula 10, the surgeon makes a small incision in the epidermis. He inserts a narrow trocar such as the trocar 70 (FIGS. 6 and 8) into the central passage 20 of the cannula 10. The pointed end portion 72 of the trocar 70 will project distally. The shaft portion 74 of the trocar 70 is disposed inside the passage 20. The outer surface 76 of the trocar shaft portion 74 engages the radially inner surfaces 60 of the wires 16. The proximal end portion 78 of the trocar 70 extends proximally from the cannula 10.

The end portion 72 of the trocar 70 may be blunt in order to push away internal tissue. In this case, a small incision would need to be made through the epidermis.

The trocar/cannula assembly is inserted through the incision in the epidermis to the subcutaneous working location. Then, a tubular insert 80 (FIG. 8) is moved distally between the wires 16 of the cannula 10 and the trocar 70. The insert 80 is preferably a hollow metal tube at least as large in ID as the OD of the trocar pointed end portion 72. The trocar 70 can then be removed from the cannula 10, leaving the cannula and the insert 80 in place in the tissue.

Figure 7:
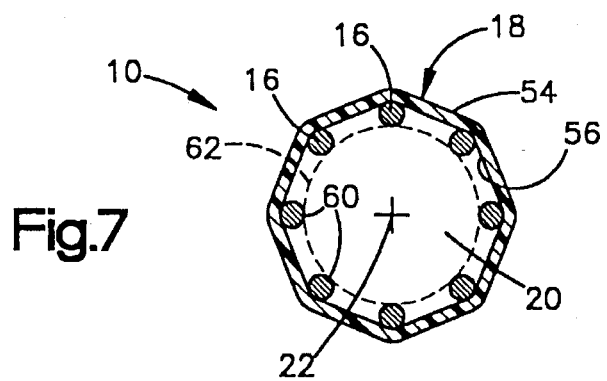
FIG. 7 is a sectional view taken along line 7—7 of FIG. 5.
Figure 8:
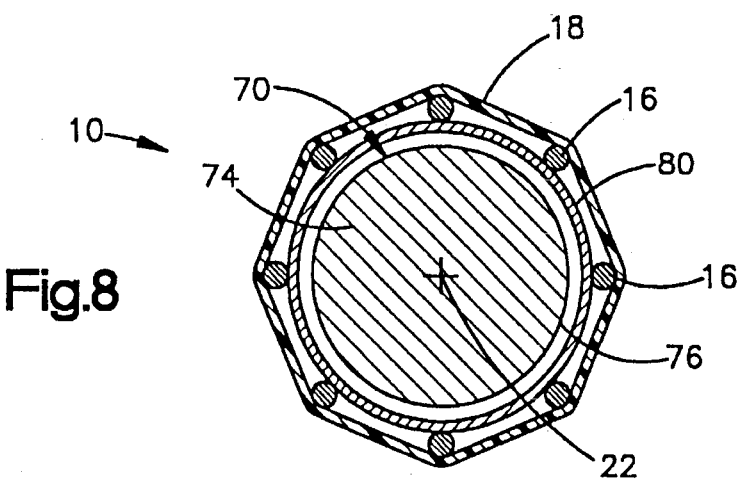
FIG. 8 illustrates the cannula of FIG. 7 in a partially expanded condition with a trocar and a tubular insert therein.

Because the insert 80 is larger in diameter than the trocar 70, during insertion of the insert 80, the cannula 10 is expanded radially outwardly, as seen in a comparison of FIGS. 7 and 8 (which are not necessarily to scale). The tissue around the cannula 10 is also stretched. The surgeon has thus made a larger passage for instruments, along its entire length, without cutting tissue.

After the tissue is allowed to relax, the surgeon removes the insert 80. The cannula 10 collapses radially inwardly because of the elastic sheath and because of the force of the tissue around it. But the tissue opening does not necessarily collapse completely, because of the viscoelastic nature of tissue, which tends to maintain its stretched condition for some time.

The surgeon then puts a second insert inside the cannula 10. The second insert is a hollow tube larger in diameter than the first insert 80. Again, the cannula expands radially outwardly, and the tissue stretches.

Figure 9:
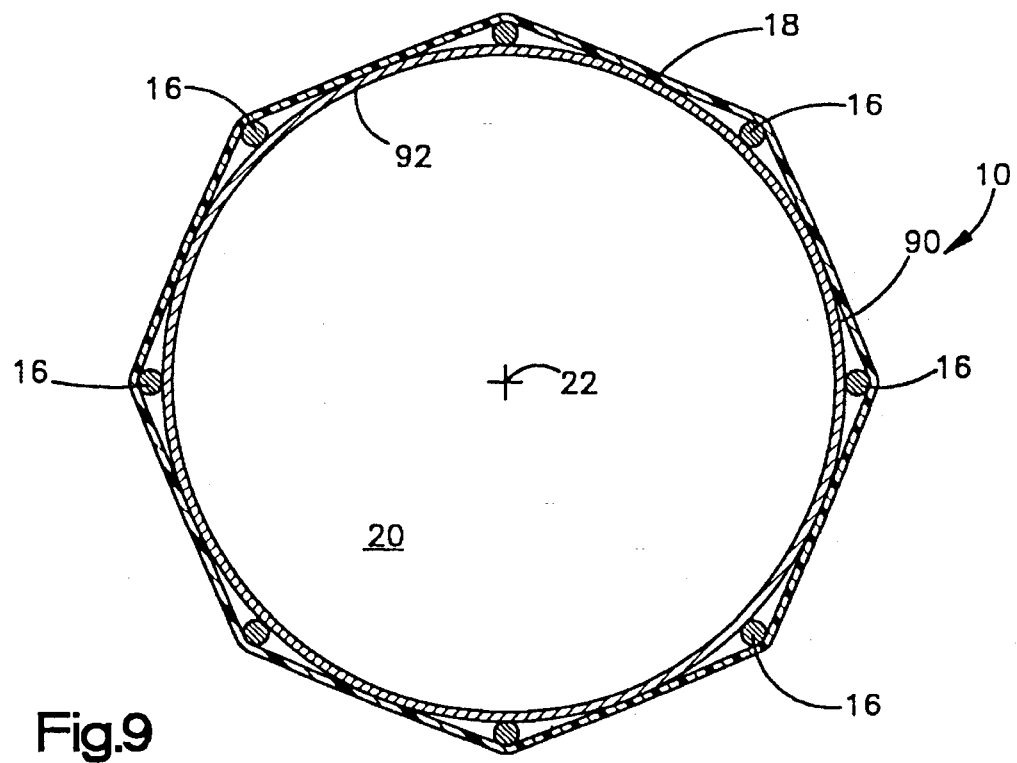
FIG. 9 illustrates the cannula of FIG. 7 in a fully expanded condition with a larger tubular insert therein.

In this manner, the surgeon continues with larger and larger inserts, until the tissue opening is as large as desired. The cannula may then be in the expanded condition shown in FIG. 9, with a full size metal insert 90 within the cannula 80. The insert 90 then functions as a normal cannula, allowing insertion and removal of surgical instruments and the like.

Figure 10:
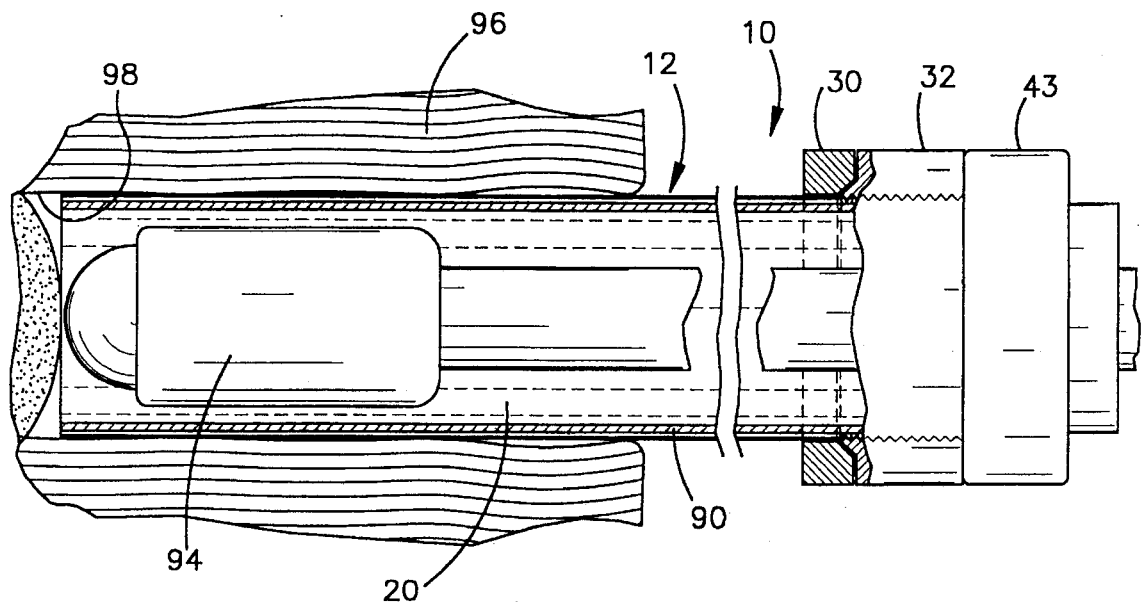
FIG. 10 illustrates the cannula of FIG. 1 in use.

Items inserted through the central passage 20 of the cannula 10 always contact the inner cylindrical surface 92 of the insert 90. This provides a non-wearing, slippery engagement, which is desirable for insertion and removal of the instruments. An example is illustrated in FIG. 10 showing a probe 94 extending through the central instrument passage 20 of the cannula 10 having an insert 90 therein. The cannula 10 has expanded tissue 96 radially outwardly to create a cavity 98 therein.

Items inserted through the central passage 20 of the cannula 10, such as the inserts 80 and 90, always contact the radially inner surfaces 60 of the wires 16. This also provides a non-wearing, slippery engagement, which is desirable for insertion and removal of the inserts.

The cannula 10 is discarded after use to prevent contamination.

Thus, it is seen that the wires 16 have outer surface portions 60 disposed radially inwardly in the cannula 10 and forming contact surfaces for surgical instruments and the like inserted through the central instrument passage 20 of the cannula. The sheath 18 has an outer circumferential surface 54 engaging tissue when the cannula 10 is in use. The wires 16 block engagement of instruments inserted through the central instrument passage 20 of the cannula 16 with the elastic sheath 18. The sheath 18 blocks engagement of tissue with the wires 16, and the sheath and the wires block engagement of tissue with any instruments inserted through the cannula 10.

The cannula 10 expands radially outwardly along substantially its entire length against the bias of the sheath 18.

Thus, the cannula 10 can accommodate through its central instrument passage 20 a surgical instrument or the like having a diameter along its entire length which is greater than the diameter of the cannula in the contracted condition. This is not possible with cannulas which expand only along a portion of their length.

A second embodiment of the invention is illustrated in FIGS. 11–17. An expandable cannula 100 includes four longitudinally extending members 102, 104, 106, and 108. Each member includes a longitudinally extending arcuate segment and a widened proximal end portion. The members 102, 104, 106, and 108 are made of plastic. One suitable material is Delrin® brand plastic.

Specifically, the member 102 includes a longitudinally extending arcuate segment 110 and a widened proximal end portion 112. The member 104 includes a longitudinally extending arcuate segment 114 and a widened proximal end portion 116. The member 106 includes a longitudinally extending arcuate segment 118 and a widened proximal end portion 120. The member 108 includes a longitudinally extending arcuate segment 122 and a widened proximal end portion 124.

The members 102, 104, 106, and 108 each subtend an angle of 90°. When the members 102, 104, 106, and 108 are placed together, their longitudinally extending arcuate segments 110, 114, 118, and 122 form a tubular expandable cannula structure 130.

The distal ends 132 of the members 102, 104, 106, and 108 are tapered inwardly for ease of entrance through tissue. The widened proximal end portions 112, 116, 120, and 124 together form a handle for the cannula 100 which also allows entry of an instrument therethrough. The end portions have angled inner surfaces 134 to guide an instrument into the longitudinally extending central instrument passage 136 of the cannula 100 in the direction indicated by the arrow 138. The handle (proximal end) portion of the cannula 100 can be configured to attach instruments to it, or to have a cap screwed onto the end to close the cannula.

Figure 11:
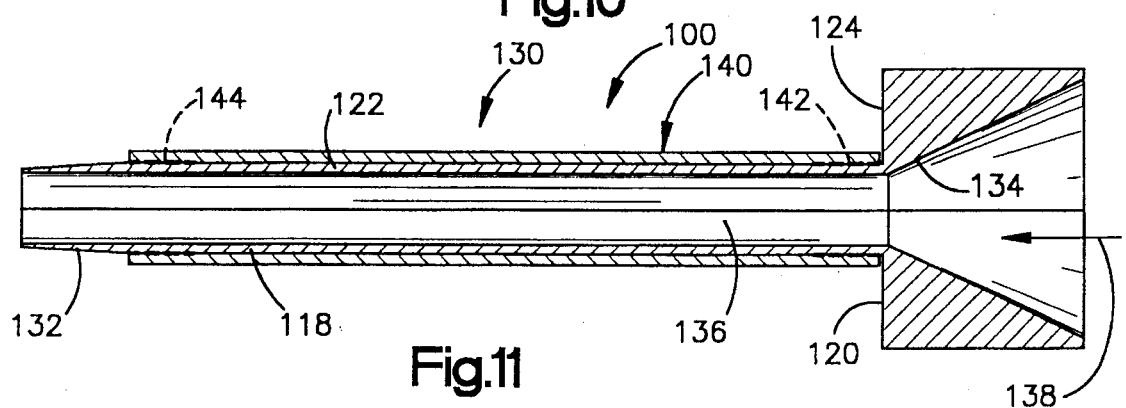
FIG. 11 is a view of a cannula in accordance with a second embodiment of the present invention, shown in an unexpanded condition.

The arcuate segments 110, 114, 118, and 122 are surrounded for most of their length by an overlying elastic sheath 140. The elastic sheath 140 may be secured to the segments 110, 114, 118, and 122 at proximal and distal locations 142 and 144 (as shown in FIG. 11), to prevent the sheath's sliding off the segments during insertion and removal of the cannula 100. Rubber cement or cyanoacrylate or a similar adhesive can be used to bond the sheath 140 to the segments Alternatively, the segments 110, 114, 118 and 122 may be free to move relative to the sheath 140 and assume the position shown in FIG. 12. The elastic sheath 140 is preferably made of latex or silicone, or of the C-Flex® material described above. The sheath 140 is of a diameter such that it is stressed even when the cannula 100 is fully contracted. Thus, the sheath 140 constantly biases the segments radially inwardly toward the center of the cannula 100.

Figures 12, 13, 14:
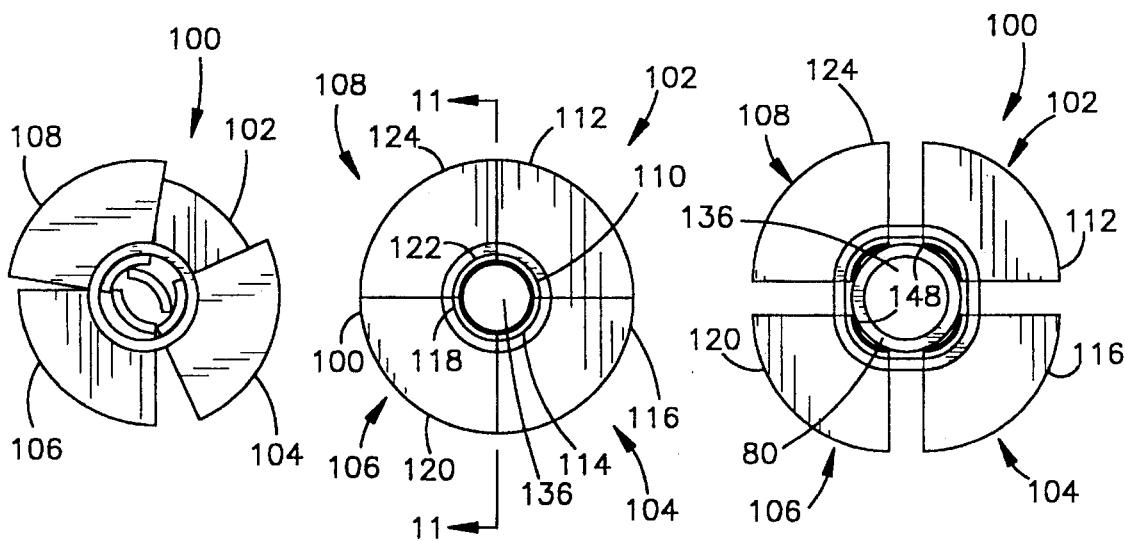
FIG. 12 is an end view of the cannula of FIG. 11 in a fully collapsed condition.
FIG. 13 is a view similar to FIG. 12 with the cannula in a partially expanded condition.
FIG. 14 is a view similar to FIG. 13 with the cannula in a fully expanded condition.
Figure 15:
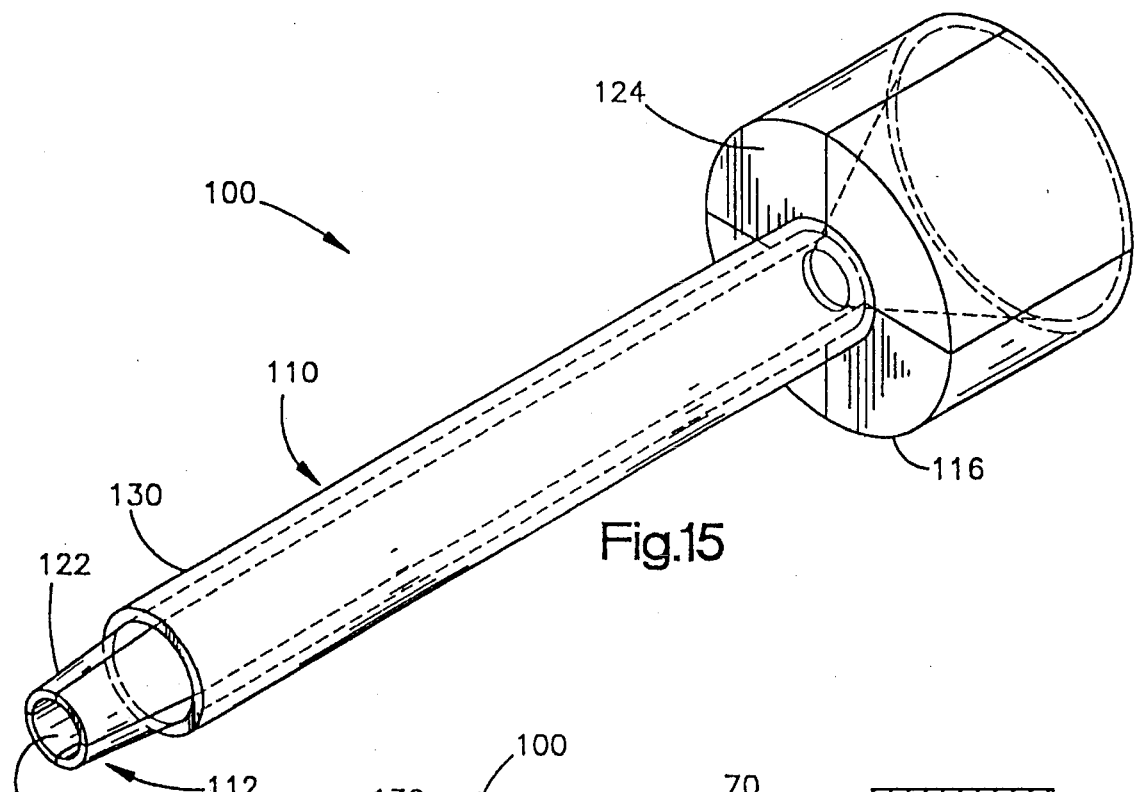
FIG. 15 is a perspective view of the cannula of FIG. 11.
Figure 16:
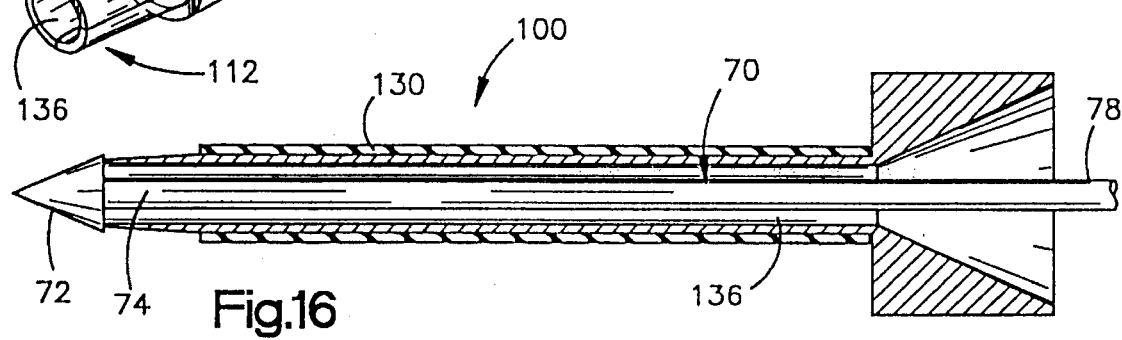
FIG. 16 illustrates the cannula of FIG. 15 with a trocar therein.
Figure 17:
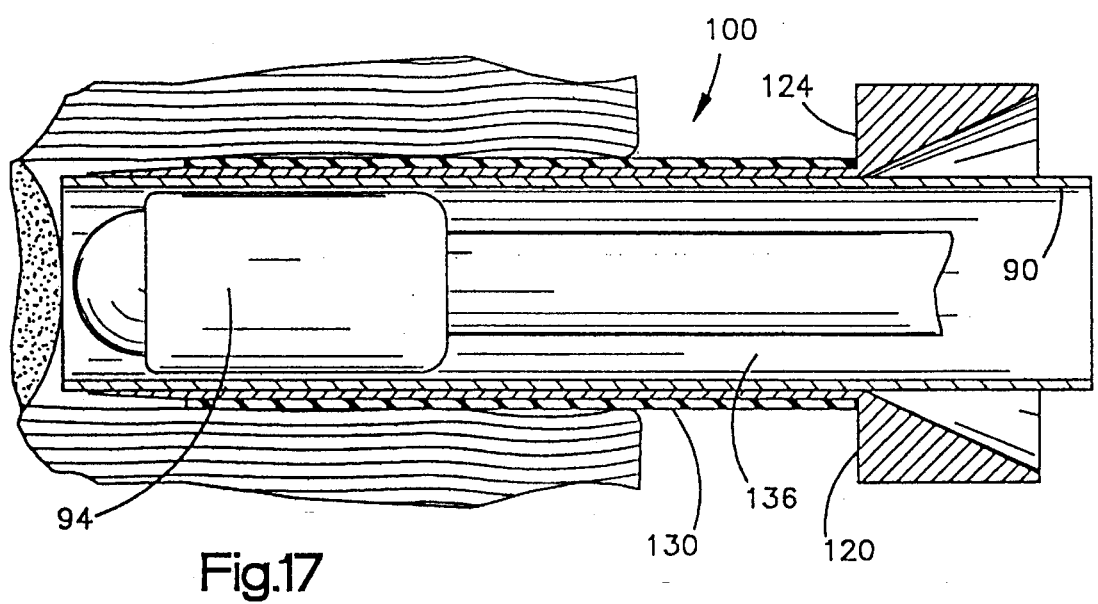
FIG. 17 illustrates the cannula of FIG. 11 in use.

One cannula that has been constructed is 90 mm in length, and about 5 mm in diameter when aligned in a tube form as shown in FIGS. 12–14. The members can collapse (overlap onto themselves as shown in FIG. 12) into a smaller diameter. The cannula can expand to about 12+mm OD.

In use of the cannula 100, the surgeon makes a small incision in the epidermis. He inserts a narrow trocar such as the trocar 70 (FIG. 16) into the central passage 136 of the cannula 100. The pointed end portion 72 of the trocar 70 will project distally. The shaft portion 74 of the trocar 70 is disposed inside the passage 136. The proximal end portion 78 of the trocar 70 extends proximally from the cannula 100.

A trocar should be used with the cannula 100 only when needed. The distal end portion of the cannula 100 is preferably used alone to push through internal tissue once an epidermal incision has been made.

The trocar/cannula assembly is inserted through the incision in the epidermis to the subcutaneous working location. Then, a tubular insert 80 (FIG. 14) is inserted longitudinally between the cannula 100 and the trocar 70. The insert 80 is preferably a hollow metal tube at least as large in ID as the OD of the trocar pointed end portion 72. The trocar 70 can then be removed from the cannula 100, leaving the cannula and the insert 80 in place in the tissue.

As the insert 80 is inserted in the cannula 100, the outer surface of the insert engages longitudinally extending radially inner edges 148 of the members 102, 104, 106, and 108. Because the insert 80 is larger in diameter than the trocar 70, during insertion of the insert, the cannula 100 is expanded radially outwardly, as seen in a comparison of FIGS. 13 and 14 (which are not necessarily to scale). The four members 102, 104, 106, and 108 move radially outwardly away from each other. The passage 136 is enlarged. The tissue around the cannula 100 is also stretched. The surgeon has thus made a larger passage for instruments, along its entire length, without cutting tissue.

After the tissue is allowed to relax, the surgeon removes the insert 80. The cannula 100 collapses radially inwardly because of the elastic sheath and because of the force of the tissue around it. But the tissue opening does not necessarily collapse completely, because the tissue is viscoelastic.

The surgeon then puts a second insert 90 (FIG. 17) inside the cannula 100. The second insert 90 is a hollow tube larger in diameter than the first insert 80. Again, the cannula 100 expands further radially outwardly, and the tissue stretches. The surgeon continues with larger and larger inserts, until the tissue opening is as large as desired. The cannula may then be in the expanded condition shown in FIG. 17, with the insert 90 within the cannula 100. The cannula 100 can then be removed proximally, leaving the insert in place. The insert then functions as a normal cannula, allowing insertion and removal of surgical instruments and the like such as the probe illustrated schematically at 94.

The cannula 100 expands radially outwardly along substantially its entire length against the bias of the sheath 130. Thus, the cannula 100 can accommodate through its central instrument passage 136 a surgical instrument or the like having a diameter along its entire length which is greater than the diameter of the cannula in the contracted condition. This is not possible with cannulas which expand only along a portion of their length.

It is contemplated that one would use two different size cannulas 100 to obtain a desired range of expansion. A first, smaller size, would extend from an OD of 2.5 mm to an ID of 7 mm, being about 70 mm in length. A second, larger size, would extend from an OD of 6 mm to an ID of 12 mm, being about 150 mm in length.

A third embodiment of the invention is illustrated in FIGS. 18–27. A rigid hollow needle 200 has a tubular wall with an inner circumferential surface and an outer circumferential surface. The needle 200 has a pointed tip 202. Proximal to the tip 202 is a radially extending opening 204 which communicates with a central passage 206 defined by the inner circumferential surface of the needle 200. The passage 206 extends to the proximal end 208 of the needle 200.

An elastic balloon 210 is bonded to the needle 200. The balloon 210 is bonded to the needle distally between the tip 200 and a rib 212 adjacent the opening 204. The balloon 210 is also bonded proximally along the needle at 214. The balloon 210 is bonded to the needle 200 so that the balloon 210 does not slide off the needle 210 during insertion and removal. The balloon 210 is preferably made of latex or silicone, or the C-Flex® material described above. The balloon 210 is of a small enough diameter such that it is stressed even when fully contracted as seen in FIG. 18. The wall thickness of the balloon 210 is exaggerated in the drawings for clarity.

Together, the needle 200 and the balloon 210 form an expandable cannula 220. The cannula 220 is inserted in tissue (not shown) to the desired location. Then the balloon 210 is inflated by the introduction of fluid under pressure through the passage 206 and the opening 204 into the interior of the balloon 210. The balloon 210 expands radially outwardly to move tissue.

The cannula 220 can be inserted (unexpanded) into the body as an ordinary needle would be used for drawing blood. The balloon 210 is then inflated to expand the surrounding tissues and create a cavity. The viscoelastic nature of the tissue allows the cavity to be maintained when the balloon 210 is rapidly deflated and the cannula 220 is removed. This cavity can then be used as an initial passage for a more conventional cannula or for an expandable cannula, and thus eliminate the need to make an initial incision. The cannula 220 has therefore without cutting tissue made an opening large enough for the passage of surgical instruments.

Alternatively, an insert (not shown) similar to the inserts 80 and 90 (FIGS. 1–9) can be slid over the expanded cannula 220. The cannula 220 can then be removed and the insert used as an ordinary cannula.

In one cannula 220 embodiment which has been constructed, the needle 200 is an 18 gauge needle, about 0.42" in diameter. The balloon 210 is about 1.25" long. The balloon 210 when unexpanded on the needle 200 is about 0.60" in diameter, and expands to about 0.315" in diameter. With appropriate material selection, there can be obtained 980% expansion (to failure) of the balloon 210.

One of a series of sleeves can be slid proximally over the cannula 220 prior to expansion to control its expansion. A few examples are illustrated in FIGS. 22–27.

A sleeve 230 (FIGS. 22 and 23) has a single arcuate segment 232 extending between circular end portions 234 and 236. The balloon 210 expands into a kidney shape at all areas between the end portions 234 and 236 other than the area covered by the segment 232. A sleeve 240 (FIGS. 24 and 25) has two arcuate segments 242 and 244 extending between circular end portions 246 and 248. The balloon 210 expands outwardly at all areas between the end portions 246 and 248 other than the areas covered by the segments 242 and 244. A sleeve 250 (FIGS. 26 and 27) has a single arcuate slot 252 extending between circular end portions 254 and 256. The balloon 210 expands outwardly only through the slot 252. Thus, it can be seen that the shape of the balloon 210 can be controlled as it expands.

The expandable cannulas of the present invention may be designed to selectively expand at a location at or near the distal end. This is illustrated in FIGS. 28–30. An expandable cannula 300 similar to the expandable cannula 10 (FIGS. 1–9) includes a plurality of longitudinally extending wires 302. Instead of an elastic sheath like the sheath 18 (FIGS. 1–9), the cannula 300 includes an inflatable sheath 304. The sheath 304 includes an inner sheath member 306 and an outer sheath member 308.

The inner sheath member 306 is of a double-walled construction, including an inner wall 310 and an outer wall 312. An inflation volume 314 separates the inner wall 310 and the outer wall 312. Fluid under pressure such as air, saline, etc. may be introduced into the inflation volume 314 through a fluid port 316. The inner sheath member 306 overlies the wires 302.

When fluid under pressure is introduced into the inflation volume 314 through the fluid port 316, the outer wall of the inner sheath member 306, expands radially outwardly as shown in FIG. 30. Radially outward expansion of the outer wall 312 of the inner sheath member 306 is limited by the outer sheath member 308. The outer sheath member 308 is a single-layer sheath overlying the inner sheath member 306. A notch 320 is cut out of the outer sheath member 308. The outer wall 312 of the inner sheath member 306 can expand radially outwardly only at the location of the notch 320 in the outer sheath member 308.

The notch 320, or any similar opening in the outer sheath member 308, may be placed at or near the distal end of the cannula 300. This will stabilize the cannula 300 in the tissue, at the closest possible location to the work area off the distal end of the cannula.

From the above description of the invention, those skilled in the art will perceive improvements, changes and modifications in the invention. Such improvements, changes and modifications within the skill of the art are intended to be covered by the appended claims.

We claim:

1. An expandable cannula having a contracted condition and being expandable from the contracted condition to an expanded condition, said expandable cannula comprising a tube having a longitudinally extending central passage for receiving surgical instruments and the like, said tube being expandable under the influence of force applied against an inner side surface of the central passage to increase the cross sectional area of the central passage upon expansion of said cannula from the contracted condition to the expanded condition, and a plurality of members enclosed by said tube, a first member of said plurality of members having an outer side surface area which is disposed in abutting engagement with the inner side surface of the longitudinally extending central passage in said tube when said cannula is in the contracted condition, a second member of said plurality of members having an outer side surface area which is at least partially spaced apart from the inner side surface of the longitudinally extending central passage in said tube when said cannula is in the contracted condition, said outer side surface areas on said members of said plurality of members being disposed in abutting engagement with the inner side surface of the longitudinally central passage in said tube when said cannula is in the expanded condition, said first member of said plurality of members having an inner side surface area and longitudinally extending edge portions which extend between said inner and outer side surface areas on said first member, said second member of said plurality of members having an inner side surface area and longitudinally extending edge portions which extend between said inner and outer side surface areas on said second member, one of said edge portions on said second member being disposed in engagement with said inner side surface area on said first member when said cannula is in the contracted condition, said one of said edge portions on said second member being disposed in engagement with one of said edge portions on said first member upon expansion of said cannula from the contracted condition.

2. An expandable cannula as set forth in claim 1 wherein said members are formed separately from each other and are movable outward away from each other for the entire length of said tube upon insertion of a dilator member into the central passage in said tube, to accommodate through the central passage a surgical instrument or the like having a cross sectional area which is greater than a cross sectional area of said central passage when said cannula is in the expanded condition.

3. An expandable cannula as set forth in claim 1 wherein said outer side surface areas on said members of said plurality of members have an arcuate configuration and have a common axis of curvature when said cannula is in the expanded condition.

4. An expandable cannula as set forth in claim 1 wherein each of said members includes a longitudinally extending portion and a widened proximal end portion, said outer side surface areas on said members being disposed on longitudinally extending portions of said members, said widened proximal end portions of said members together forming a handle portion of said expandable cannula.

\* \* \* \* \*